United States Patent [19]

Schrock

[11] Patent Number: 4,812,588

[45] Date of Patent: Mar. 14, 1989

[54] POLYORGANOSILOXANE-BRIDGED BISBENZOCYCLOBUTENE MONOMERS

[75] Inventor: Alan K. Schrock, Lake Jackson, Tex.

[73] Assignee: The Dow Chemical Company, Midland, Mich.

[21] Appl. No.: 132,734

[22] Filed: Dec. 14, 1987

[51] Int. Cl.$^4$ .............................. C07F 7/08; C07F 7/10
[52] U.S. Cl. ...................................... 556/453; 556/415; 556/416; 556/417; 556/445; 556/446; 556/454
[58] Field of Search ............... 556/415, 416, 417, 445, 556/446, 453, 454

[56] References Cited

U.S. PATENT DOCUMENTS

| | | | |
|---|---|---|---|
| 2,611,774 | 9/1952 | Tyler | 556/453 |
| 4,536,950 | 8/1985 | Brown | 556/453 |
| 4,540,763 | 9/1985 | Kirchhoff | 526/281 |

*Primary Examiner*—Paul F. Shaver

[57] ABSTRACT

Bisbenzocyclobutene monomers bridged by a polyorganosiloxane group. The monomers are liquid at room temperature.

6 Claims, No Drawings

POLYORGANOSILOXANE-BRIDGED BISBENZOCYCLOBUTENE MONOMERS

The U.S. Government has a paid-up license in this invention and the right in limited circumstances to require the patent owner to license others on reasonable terms as provided for by the terms of contract No. F33615-85-C-5092 awarded by Wright-Patterson Air Force Base.

BACKGROUND OF THE INVENTION

This invention relates to bisbenzocyclobutene monomers. More specifically, it relates to bisbenzocyclobutene monomers bridged by a polyorganosiloxane group.

Polymers derived from bisbenzocyclobutene monomers are disclosed in U.S. Pat. No. 4,540,763. The polymers are prepared by subjecting bisbenzocyclobutene monomers to temperatures sufficient for polymerization. The polymers exhibit excellent thermal stability at high temperatures, good chemical resistance to most industrial solvents, good physical and mechanical properties, and low sensitivity to water. The polymers are useful for preparing composites, coatings and films; and as adhesives.

Unfortunately, the bisbenzocyclobutene monomers from which the polymers of U.S. Pat. No. 4,540,763 are derived are solids at room temperature. Therefore, for numerous applications, the monomers must be melted at high temperatures, which may be as high as 200° C., or dissolved in solvents before processing can occur. This requires an extra processing step that can be time-consuming and expensive. Furthermore, solvents required to dissolve the monomer must be removed before the final curing step, which may create voids within the polymer.

In view of the deficiencies of the prior art, a liquid bisbenzocyclobutene monomer is needed. In addition, a bisbenzocyolobutene monomer that can be processed at room temperature without requiring a solvent to dissolve the monomer is needed.

SUMMARY OF THE INVENTION

The invention is a bisbenzocyclobutene monomer of the formula:

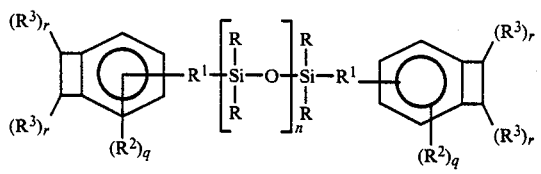

wherein
  each R is independently alkyl of 1 to 6 carbon atoms, cycloalkyl, aralkyl, or phenyl:
  each $R^1$ is independently vinyl, allyl, or methallyl;
  each $R^2$ is independently alkyl of 1 to 6 carbon atoms, methoxy, or chloro:
  each $R^3$ is independently alkyl of 1 to 6 carbon atoms, chloro, or cyano:
  n is an integer of 1 or more: and
  each q and r is independently an integer of zero or 1.

The monomer is a liquid at room temperature. Therefore, it requires neither high temperature processing to melt the monomer nor solvents to dissolve the monomer. The monomers are particularly useful for preimpregnating fibers for the preparation of fiber-reinforced composites, and for preparing coatings and adhesives, particularly for electronics applications.

DETAILED DESCRIPTION OF THE INVENTION

The bisbenzocyclobutene monomers of this invention are monomers bridged by an organopolysiloxane group. The monomers are represented by the formula:

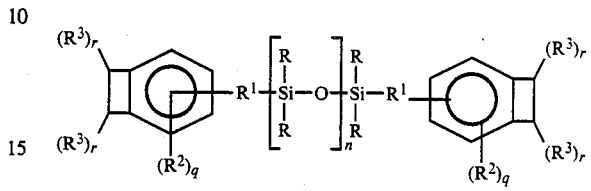

wherein
  each R is independently alkyl of 1 to 6 carbon atoms, cycloalkyl, aralkyl, or phenyl:
  each $R^1$ is independently vinyl (—CH=CH—), allyl (—CH=CH—CH$_2$—), or methallyl

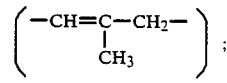

each $R^2$ is independently alkyl of 1 to 6 carbon atoms, methoxy, or chloro;
  each $R^3$ is independently alkyl or 1 to 6 carbon atoms, chloro, or cyano;
  n is an integer of 1 or more; and
  each q and r is independently an integer of zero or 1.

The preferred alkyl group is methyl and preferred monomers are represented by the formula:

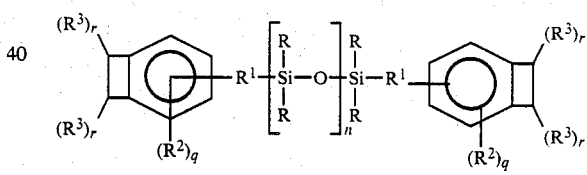

wherein
  each R is independently methyl, cycloalkyl, aralkyl, or phenyl;
  each $R^1$ is independently vinyl, allyl, or methallyl;
  each $R^2$ is independently methyl, methoxy, or chloro;
  each $R^3$ is independently methyl, ohloro, or cyano;
  n is an integer between 1 and 4500, inclusive: and
  each q and r is independently an integer of zero or 1.

More preferred monomers are represented by the formula:

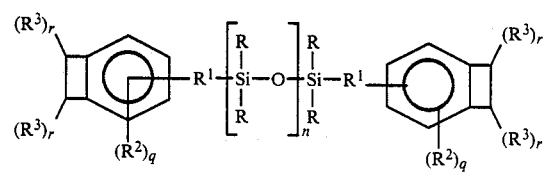

wherein
  each R is independently methyl, cycloalkyl, aralkyl, or phenyl;
  each $R^1$ is independently vinyl, allyl, or methallyl:

each R² is independently methyl or chloro;
R³ is chloro;
n is an integer between 1 and 4500, inclusive: and
each q and r is independently an integer of zero or 1.

Preferably, the benzoyclobutene groups of the monomers are unsubstituted and the monomers are represented by the formula:

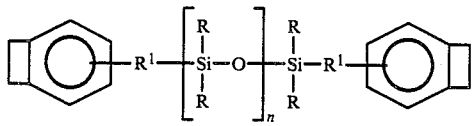

wherein
each R is independently methyl, cycloalkyl, or phenyl;
each R¹ is independently vinyl, allyl, or methallyl; and
n is an integer between 1 and 10, inclusive.

More preferred monomers are represented by the formula:

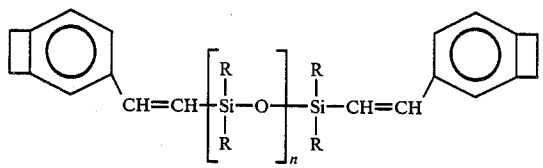

wherein
each R is independently methyl or phenyl, and
n=1, 2 or 3.

The most preferred monomer is represented by the formula:

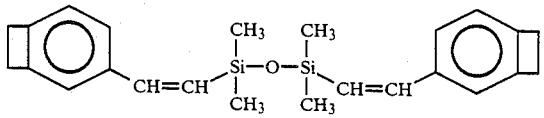

The bisbenzocyclobutene monomers of this invention can be prepared by reacting a bromobenzocyclobutene with the desired organopolysiloxane bridging group. The reaction is possible because the organopolysiloxane bridging group is a bisvinyl or bisallyl bridging group. The substitution reaction of an olefinic compound possessing at least one hydrogen on a vinylic position with an organic halide is known and disclosed in U.S. Pat. No. 3,922,299 (Heck), which is incorporated by reference herein.

Heck discloses the substitution reaction of aryl halides with olefinic compounds in the presence of a Group VIII metal, a trivalent arsenic or phosphorous compound, and a soluble trialkylamine. The reaction displaces a hydrogen on a vinylic or allylic position with the organic compound. For example, the most preferred bisbenzocyclobutene monomer can be prepared by reacting about 2 moles of bromobenzocyclobutene with about one mole of 1,3-divinyl-1,1,3,3-tetramethyl-disiloxane in the presence of a catalytic amount of palladium acetate and tri(ortho-tolyl)phosphine, in addition to triethylamine, which acts as an acid scavenger.

Organopolysiloxanes and processes for preparing them are known and disclosed in U.S. Pat. Nos. 3,584,027; 3,701,195: 3,770,768: and 3,803,196. A process for preparing bromobenzocyclobutene is disclosed by Lloyd et al., *Tetrahedron*. Vol. 21, pp. 245-254 (1965) at page 253.

The following example is illustrative and does not limit the scope of this invention.

EXAMPLE 1 A solution of 3.0 grams (g) ($1.64 \times 10^{-2}$m) 4-bromobenzocyclobutene, 1.52 g ($8.2 \times 10^{-3}$m) 1,3-divinyl-1,1,3,3-tetramethyldisiloxane. 1.66 g ($1.64 \times 10^{-2}$m) triethylamine, 0.152 g ($5.0 \times 10^{-4}$m) tri-o-tolylphosphine, 72 milligrams (mg) ($3.21 \times 10^{-4}$m) palladium (II) acetate, and 10 mL acetonitrile in a 50 mL 2-neck round bottom flask equipped with a reflux condenser and magnetic stirring bar is heated to reflux for 24 hours. After 24 hours, the reaction mixture is cooled to room temperature and then poured into 60 mL 10 percent aqueous hydrochloric acid. The resulting mixture is extraoted with two 50 mL portions of methylene chloride and the combined methylene chloride solutions are washed with three 100 mL portions of water. The organic phase is dried over anhydrous magnesium sulfate, filtered, and evaporated in vacuo to yield a yellow oil. The oil is chromatographed on silioa gel eluting with 20 percent toluene in heptane. The product is removed from the column and the solvent removed to yield a colorless oil. Reverse phase high performance liquid chromatography shows a mixture with one major component. ¹H-NMR (CDCl₃) 7.3–6.1 (m, 10H), 3.2 (s, 8H), 0.2 (s, 12H) ppm A sample of the product mixture is poured into a mold and polymerized by heating the mold slowly to 250° C. The resulting polymer is removed from the mold as a clear, hard, void-free part. Another sample of the product mixture is poured onto the surface of a substrate, leveled, and cured to form a clear flexible coating. The polymers prepared in this manner show weight loss onsets as measured by thermogravimetric methods near 400° C., providing evidence of high temperature usefulness.

Upon repeating the procedures of this example with varying substituted or unsubstituted bromobenzocyclobutenes and varying organopolysiloxane bridging groups, other bisbenzcoyclobutene monomers within the scope of this invention can be prepared.

What is claimed is:
1. A bisbenzocyclobutene monomer represented by the formula:

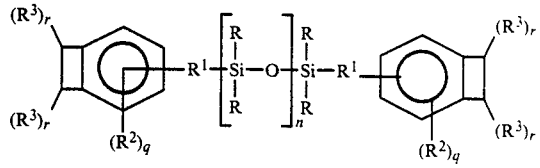

each R is independently alkyl of 1 to 6 carbon cycloalkyl, aralkyl, or phenyl:
each R¹ is independently vinyl, allyl, or methallyl:
each R² is independently alkyl of 1 to 6 carbon atoms, methoxy, or chloro;
each R³ is independently alkyl of 1 to 6 carbon atoms, chloro, or cyano:
n is an integer of 1 or more; and
each q and r is independently an integer of zero or 1.

2. The bisbenzocyclobutene monomer of claim 1 represented by the formula:

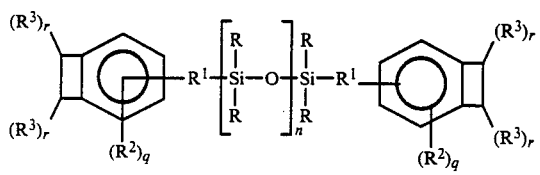

wherein
  each R is independently methyl, cycloalkyl, aralkyl, or phenyl;
  each $R^1$ is independently vinyl, allyl, or methallyl;
  each $R^2$ is independently methyl, methoxy, or each $R^3$ is independently methyl, chloro, or
  n is an integer between 1 and 4500, inclusive: and
  each q and r is independently an integer of zero or 1.

3. The bisbenzocyclobutene monomer of claim 2 represented by the formula:

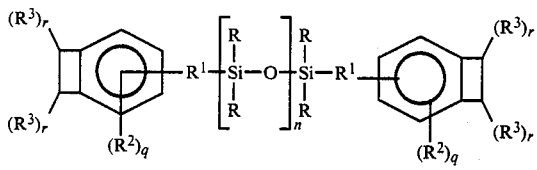

wherein
  each R is independently methyl, cycloalkyl, aralkyl, or phenyl;
  each $R^1$ is independently vinyl, allyl, or methallyl;
  each $R^2$ is independently methyl or chloro;
  $R^3$ is chloro;
  n is an integer between 1 and 4500, inclusive; and
  each q and r is independently an integer of zero or 1.

4. The bisbenzocyclobutene monomer of claim 3 represented by the formula:

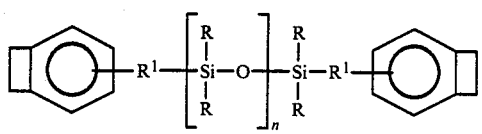

wherein
  each R is independently methyl, cycloalkyl, or phenyl;
  each $R^1$ is independently vinyl, allyl, or methallyl; and
  n is an integer between 1 and 10, inclusive.

5. The bisbenzocyclobutene monomer of claim 4 represented by the formula:

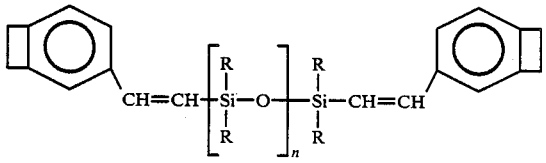

wherein
  each R is independently methyl or phenyl, and
  n=1, 2, or 3.

6. The bisbenzocyclobutene monomer of claim 5 represented by the formula:

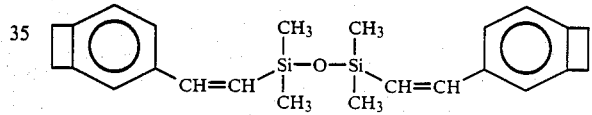

* * * * *